US00PP17136P3

(12) United States Plant Patent
Houbraken

(10) Patent No.: US PP17,136 P3
(45) Date of Patent: Oct. 10, 2006

(54) ***ARGYRANTHEMUM FRUTESCENS* PLANT NAMED 'ARGYMONWI'**

(50) Latin Name: *Argyranthemum frutescens*
Varietal Denomination: Argymonwi

(75) Inventor: Annemarie Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 156 days.

(21) Appl. No.: 10/920,095

(22) Filed: Aug. 17, 2004

(65) Prior Publication Data

US 2006/0041968 P1 Feb. 23, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Bruce Vrana

(57) ABSTRACT

A distinct cultivar of *Argyranthemum frustescens* plant named 'Argymonwi' characterized by its compact ball shaped plant habit, good field performance, white single flowers, dark green coloured leaves, freely flowering with numerous inflorescences per plant.

1 Drawing Sheet

Latin name of the genus and species of the plant claimed: *Argyranthemum frutescens.*
Varietal denomination: 'Argymonwi'.

BACKGROUND OF THE NEW PLANT

The present invention relates to a new and distinct cultivar of Marguerite Daisy plant, botanically known as *Argyranthemum frutescens* and referred to by the cultivar name 'Argymonwi'. The new cultivar is a product of a planned breeding program conducted by the inventor in Enkhuizen, The Netherlands. The objective of the breeding program was to develop a more compact plant that flowers early and can be grown without growth regulators.

DESCRIPTION OF THE DRAWING

This new Marguerite Daisy plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Marguerite Daisy plant. The data which defines these characteristics were collected from asexual reproductions by terminal cuttings taken in a controlled environment in Enkhuizen, the Netherlands, since Aug. 1, 2001, has shown that the unique features of this new *Argyranthemum* are stable and reproduced true to type in successive generations. The plant history was taken on 25 weeks old plants, grown in the field in Enkhuizen, The Netherlands with day temperatures ranging from 16 to 30 degree C., and night temperatures ranging from 10 to 16 degrees Celsius.

Color references are primarily to The R.H.S. Color Chart of The Royal Horticultural Society of London where general terms of ordinary dictionary significance are used.

TABLE 1

Differences between the new cultivar 'Argymonwi' and two similar cultivars

| | 'Argymonwi' | 'White Star' (Unpatented) | 'Sugar Baby' (U.S. Plant Patent No. 10,298) |
|---|---|---|---|
| Plant Height | 28–29 cm | 35 cm | 25–27 cm |
| Plant Width | 25–30 cm | 50–55 cm | 55–60 cm |
| Flower diameter | 2.2–2.6 cm | 1.5–2 cm | 2–3 cm |
| Foilage color | 144A | 144C fading to 4A | 144A fading to 12A |
| Flower stem length | 2–4 cm | 4 cm | 5 cm |

The plant:

*Classification.*—Botanical: *Argyranthemum frutescens* cv. 'Argymonwi'.

Parentage:

*Female parent.*—Proprietary seedling section of *Argyranthemum frutescens,* identified as number B8. Breeder's code of the new plant 'Argymonwi' is C 101-16 (unpatented).

*Male parent.*—Unidentified section of *Argyranthemum frutescens* (unpatented).

Propagation:

*Type cuttings.*—Terminal cuttings.

*Time to intiated roots.*—7–10 days at air temperature of 21 degrees C.

*Time to develop roots.*—7–14 days at air temperature of 18 degrees C.

Plant description:

*Growth habit.*—Ball shape.

*Plant height.*—28 cm.

*Vigor.*—Compact.

*Speading area of plant.*—25–30 cm.

*Strength.*—Very good.

*Branching character.*—Freely branching, plants do not require pinching.

*Crop time.*—About 9 weeks are required to produce a finished flowering plant in a 10.5 cm container from a good developed cutting.

The stem:

*Diameter.*—4 mm.
*Shape.*—Round, bit grooved.
*Anthocyanin pigmentation.*—Absent.
*Length of internode.*—2–3 cm.
*Pubescence.*—Absent.
*Color.*—143B.

The foliage:

*Arrangement.*—Alternate.
*Shape of leaf.*—Bipinnatisect.
*Leaf apex.*—Acute.
*Leaf base.*—Attenuate.
*Texture.*—Thick glabrous smooth.
*Length.*—3–3.5 cm.
*Width.*—0.6–1 cm.
*Leaf margin.*—Lanciniate.
*Depth of incision.*—4–15 mm.
*Color.*—Upper side: 144A. Lower side: 144A. Old leaf 146C.
*Pubescence.*—Absent.
*Petiole.*—Absent.
*Venation.*—Shape: Pinnate. Color: 138A.

Flower bud:

*Peduncle.*—Length: 2–4 cm. Strength: Strong. Texture: Smooth. Color: 143A.
*Size of the bud.*—Length: 3 mm. Diameter: 3–5 mm.
*Shape.*—Flattened, round.
*Color.*—199A.

Inflorescence:

*Diameter.*—2.2–2.6 cm.
*Form.*—Single flowered.
*Receptacle height.*—0.3 cm.
*Involucre/phyllaries.*—3 series of 5 bracts, tightly to receptacle. Shape: Elliptic, with broad apex. Margin: Entire. Length: 3–4 mm. Color: Upper: 137B. Lower: 144B.
*Fragrance.*—Absent.
*Quantity of inflorescences.*—400 flower/plant depending on age and growing conditions.
*Flowering period.*—April til October in N-W Europe, plants flower continuously.

Ray florets:

*Shape of ray florets.*—Ligulate.
*Apex.*—Rounded, little incised.
*Base.*—Cordate.
*Margin.*—Entire.
*Color.*—155B.
*No. of ray florets per inflorescene.*—16–18.
*Size.*—Length: 1.2–1.4 cm. Width: 0.4–0.5 cm.
*Texture: Smooth.*

Disc florets:

*Shape of disc florets.*—Tubular (trumpet shape) with 5 lobes.
*Color.*—12A.
*Diameter of disc floret.*—1 mm.
*Length of disc floret.*—4 mm.
*Number of disc florets/flower.*—±80.

Androecium:

*Anther color.*—Yellow 12A.
*Pollen color.*—Yellow 12A.
*Amount of pollen.*—Only in disc florets, little pollen.

Gynoecium:

*Pistil number.*—One per floret (ray florets only).
*Pistil length.*—±3 mm.
*Style color.*—Yellow green 144D.
*Style length.*—±1 mm.
*Stigma color.*—Yellow orange 14A.
*Stigma shape.*—Bilobed.
*Ovary color.*—144C.

Seed: Seed production is not observed.

Disease resistance: No susceptibility nor resistance to fungal, bacterial or viral pathogens has been noted. Material is free of virus and *Chrysanthemum* stunt viroid (CSVd).

What is claimed is:

1. A new and distinct variety of *Argyranthemum frutescens* plant, substantially as herein illustrated and described.

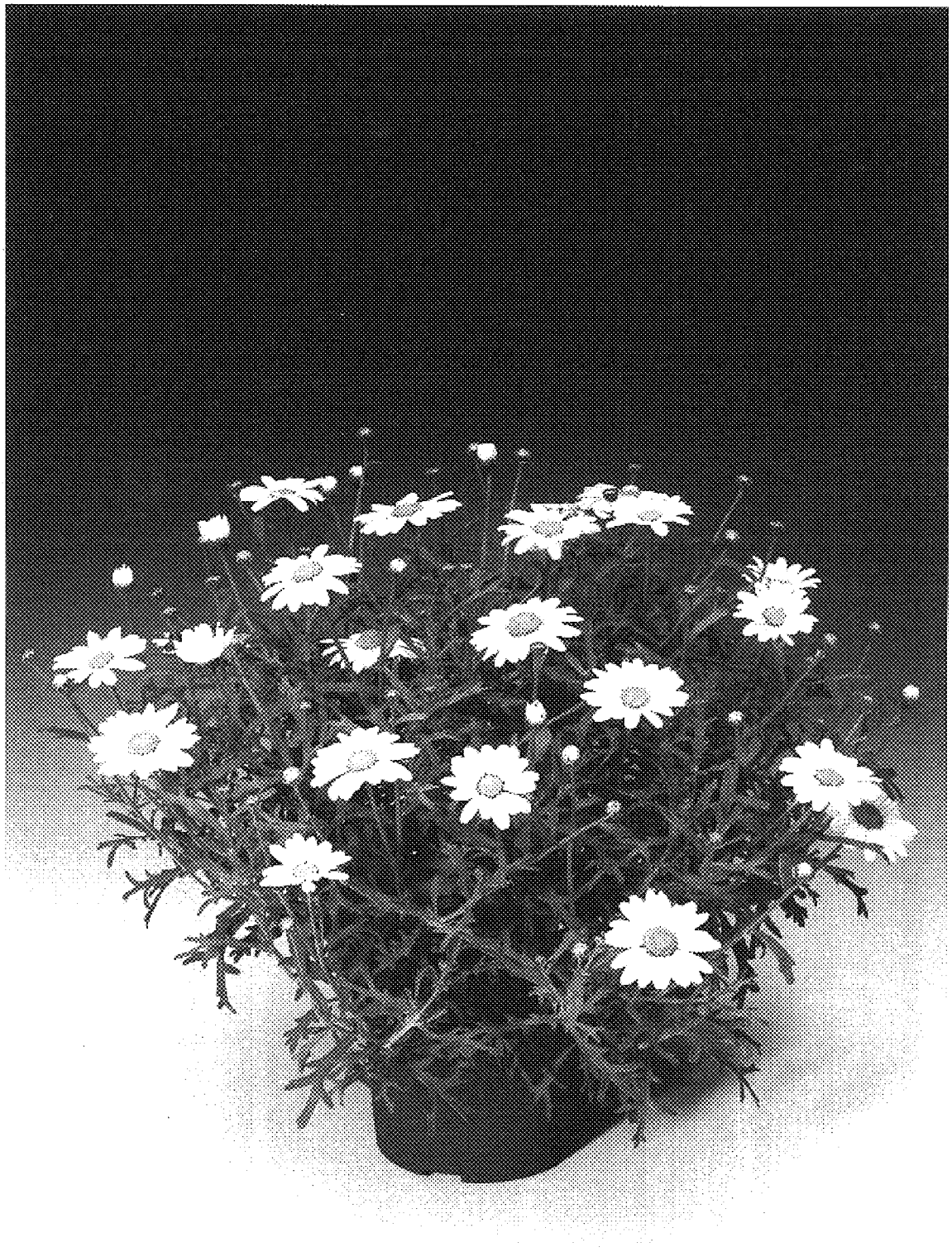

* * * * *